United States Patent
Goldbach (10) Patent No.: US 8,446,473 B2
(45) Date of Patent: May 21, 2013

(54) TRACKING SYSTEM WITH SCATTERING EFFECT UTILIZATION, IN PARTICULAR WITH STAR EFFECT AND/OR CROSS EFFECT UTILIZATION

(75) Inventor: Günter Goldbach, Forstinning (DE)

(73) Assignee: Brainlab AG, Feldkirchen (DE)

( * ) Notice: Subject to any disclaimer, the term of this patent is extended or adjusted under 35 U.S.C. 154(b) by 2313 days.

(21) Appl. No.: 11/244,662

(22) Filed: Oct. 5, 2005

(65) Prior Publication Data

US 2006/0089552 A1   Apr. 27, 2006

Related U.S. Application Data

(60) Provisional application No. 60/618,855, filed on Oct. 14, 2004.

(30) Foreign Application Priority Data

Oct. 5, 2004   (EP) .................................... 04023719

(51) Int. Cl.
    *H04N 5/225*   (2006.01)
    *H03K 19/096*   (2006.01)
    *A61B 8/00*   (2006.01)

(52) U.S. Cl.
    USPC .............................. 348/172; 326/96; 600/439

(58) Field of Classification Search ................. 348/135, 348/169–172; 326/96; 600/439; 382/103, 382/107

See application file for complete search history.

(56) References Cited

U.S. PATENT DOCUMENTS

| | | | | |
|---|---|---|---|---|
| 4,696,574 A | * | 9/1987 | Penney | 356/614 |
| 5,197,476 A | | 3/1993 | Nowacki et al. | |
| 5,333,044 A | * | 7/1994 | Shaffer | 356/28 |
| 5,383,454 A | | 1/1995 | Bucholz | |
| 5,640,241 A | * | 6/1997 | Ogawa | 356/615 |
| 5,642,164 A | * | 6/1997 | Ogawa | 348/335 |

(Continued)

FOREIGN PATENT DOCUMENTS

| | | |
|---|---|---|
| DE | 196 39 615 A1 | 4/1998 |
| DE | 10 056 186 A1 | 5/2002 |

(Continued)

OTHER PUBLICATIONS

European Search Report for corresponding Application No. 04023719.0 dated Jan. 26, 2005.

*Primary Examiner* — Lin Ye
*Assistant Examiner* — Chia-Wei A Chen
(74) *Attorney, Agent, or Firm* — Renner, Otto, Boisselle & Sklar, LLP (57) ABSTRACT

An image generating device for an optical, in particular medical tracking system, for determining the position of a recorded image point, includes a light scattering effect generating device, in particular a star and/or cross effect generating device. The invention further provides a tracking system including such an image generating device and to a method for determining the position of a recorded image point using an optical, in particular medical tracking system, in which: an image is generated using an image generating device; a light scattering effect, in particular a star and/or cross effect, is generated on the image for predetermined image points; and in which the position of an image point is ascertained on the basis of the light scattering pattern projected on the image, in particular on the basis of the star and/or cross effect lines and/or their intersection points.

17 Claims, 5 Drawing Sheets

U.S. PATENT DOCUMENTS

| | | | |
|---|---|---|---|
| 5,815,590 A * | 9/1998 | Buttner et al. | 382/103 |
| 5,828,770 A | 10/1998 | Leis et al. | |
| 5,831,735 A | 11/1998 | Corby, Jr. | |
| 5,921,992 A | 7/1999 | Costales et al. | |
| 5,928,140 A | 7/1999 | Hardten | |
| 6,324,296 B1 * | 11/2001 | McSheery et al. | 382/107 |
| 6,351,659 B1 | 2/2002 | Vilsmeier | |
| 6,437,820 B1 | 8/2002 | Josefsson | |
| 6,484,049 B1 | 11/2002 | Seeley | |
| 6,490,475 B1 | 12/2002 | Seeley | |
| 6,493,095 B1 | 12/2002 | Song et al. | |
| 7,366,420 B2 * | 4/2008 | Yoshimi et al. | 398/129 |
| 2002/0095081 A1 | 7/2002 | Vilsmeier | |
| 2003/0099435 A1 | 5/2003 | Yang | |
| 2003/0174401 A1 | 9/2003 | Brunner et al. | |
| 2003/0181800 A1 | 9/2003 | Bonutti | |
| 2003/0225329 A1 | 12/2003 | Rossner et al. | |
| 2004/0122311 A1 | 6/2004 | Cosman | |
| 2005/0063606 A1 * | 3/2005 | Kita | 382/260 |
| 2005/0190987 A1 * | 9/2005 | Schulz | 382/291 |

FOREIGN PATENT DOCUMENTS

| | | |
|---|---|---|
| WO | 97/47240 | 12/1997 |
| WO | 00/16121 | 3/2000 |
| WO | 03/038481 A1 | 5/2003 |
| WO | 2004/078039 A1 | 9/2004 |

* cited by examiner

TRACKING SYSTEM WITH SCATTERING EFFECT UTILIZATION, IN PARTICULAR WITH STAR EFFECT AND/OR CROSS EFFECT UTILIZATION

RELATED APPLICATION DATA

This application claims priority of U.S. Provisional Application No. 60/618,855 filed on Oct. 14, 2004, which is incorporated herein by reference in its entirety.

FIELD OF THE INVENTION

The invention relates generally to tracking systems and, more particularly, to an image generating system, apparatus and method for use with an optical tracking system, such as a medical tracking system or the like, for determining a position of a recorded image point.

BACKGROUND OF THE INVENTION

Conventional optical tracking systems and their image generating devices generally include a pair of cameras that record individual image points. These image points, which typically comprise positional markers and/or natural landmarks, are used to detect information on a position (e.g., the spatial position of the image points) from a stereoscopic image obtained from the cameras. Thus, there are existing systems that include an image processing unit within the camera system. These existing systems can provide spatial coordinates of detected image points, which then can be provided as an output signal. In principle, however, the images can also be processed externally.

Examples of generic tracking systems that perform optical three-dimensional surveying may be found in the following documents, the contents of which are hereby incorporated by reference in their entirety: DE 10 056 186 A1; U.S. Pat. No. 5,831,735; U.S. Pat. No. 6,493,095 B1; U.S. Pat. No. 6,437,820 B1; U.S. Pat. No. 5,828,770 and WO 00/16 121.

Within the medical field, optical tracking systems, for example, are presented in the following documents, the contents of which are hereby incorporated by reference in their entirety: U.S. Pat. No. 6,351,659 B1 or DE 19 639 615 C2; U.S. Pat. No. 6,484,049 B1 or U.S. Pat. No. 6,490,475 B1 (fluoroscopic tracking system) and U.S. Pat. No. 5,921,992.

Figure 4A:
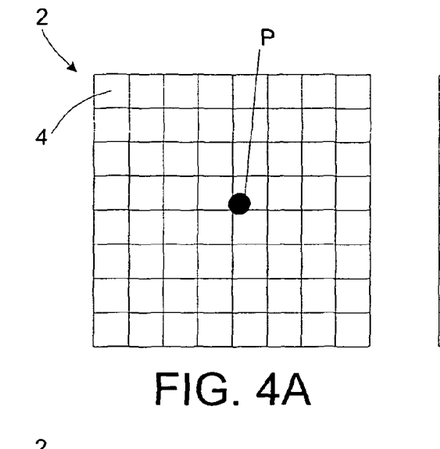
FIGS. 4A-4F illustrate a contrast between ascertaining the position of the image points using a conventional approach and using light scattering effects in accordance with an embodiment of the invention.
Figure 4B:
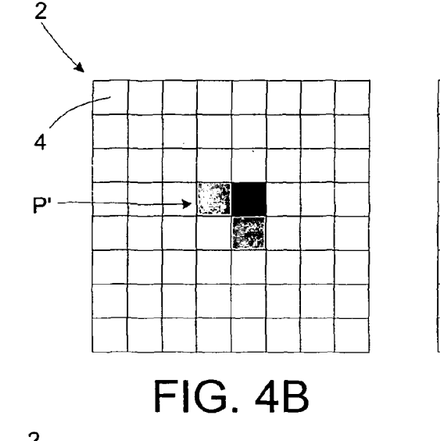
Figure 4C:
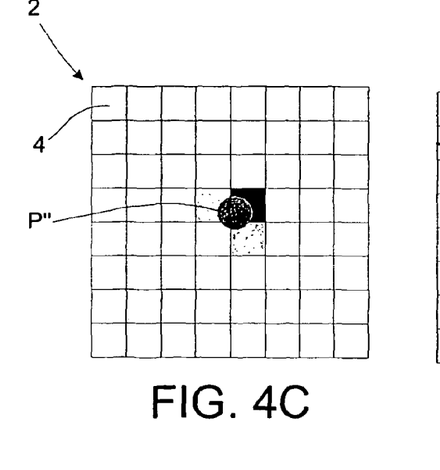

Conventional tracking systems, which use camera systems having a predetermined image resolution, have the disadvantage that their position determining accuracy is substantially dependent on the resolution of the image generating devices. If relatively small markers or landmarks are to be recorded and their position determined, or in the case of markers and/or landmarks that are relatively far away from the image generating device, the accuracy of conventional image generating devices quickly reaches its limits. For example, FIGS. 4A-4C show how an image point P would be positionally detected on an 8×8 sensor 2 of a conventional image generating device. It is noted that the size of the image points (e.g. a marker) on the sensor 2 can be much smaller than a pixel 4 of the sensor 2, which in this conventional scenario results only in a maximum positional accuracy of one pixel.

More specifically, FIGS. 4A-4C illustrate an image point P spanning four pixels 4 of the sensor 2 and, therefore, exposing the four pixels 4 with different intensities within its projection P' (FIG. 4B). Interpolating the "brightness" (e.g., the developing or illuminating intensity) of the group of pixels results in a sub-pixel resolution that ascertains a "focus" of the projection P', which is approximately in the area of the actual image point P. Thus, the position of the point P can be calculated to be approximately at the point P" as shown in FIG. 4C.

Such sub-pixel resolution is only possible when the image point P actually exposes more than one pixel 4. In the worst case scenario (i.e., wherein the image point P is within a single pixel), the image point position only can be determined as being within that pixel 4. Thus, in the case of small markers or image points having a size less than one pixel 4, a significant error can arise.

Accordingly, the accuracy of the conventional optical system can be determined by the resolution of the sensor 2 and the dynamics and linearity of the sensor pixel 4 (and in the 3D scenario, by the homogeneity of the marker). In the case of medical tracking systems or other tracking systems, which in many cases depend on accuracies of fractions of millimeters, an accuracy error of one pixel typically cannot be tolerated. Hence, attempts have been made to make markers as large as possible, thereby enabling one to determine the marker position by averaging a number of exposed pixels 4.

In other words, the size of markers and their maximum distance from the image generating device can be determined by a resolution and a reproduction scale of the lenses. While the size of image points could be increased simply by using larger markers, larger markers would incur significant disadvantages related to handling, cost and weight of the markers.

Furthermore, several other preconditions should be fulfilled in conventional systems in order to determine the position of such image points, namely:

- pixel exposure should be triggered only by a single object, otherwise the weighting of grey scales for the sub-pixel resolution can be off;
- the focus should be the interpolated center for the brightness (this is not the case if a marker is partially hidden, is not round or is tarnished, or if the reflecting surface is not projected with a uniform brightness);
- if viewed from two different angles, a round marker should produce the same image on two sensors (this is likewise not the case if the marker is not round, is tarnished or partially hidden, or if the brightness of the reflecting surface is not homogenous);
- the image of the marker should be large enough to cover at least one pixel (in practice, at least four pixels); and
- the marker should be bright enough to be distinguishable from background noise.

All of these assumptions and restrictions incur disadvantages for conventional tracking systems. Attempts have been made to solve these problems by using image generating devices with ever higher resolutions. However, very high resolution image generating devices are also very expensive and, therefore, significantly increase costs. Also, some of the above problems cannot be solved simply by using exceedingly high resolution image generating devices. For example, when image points are not completely visible, e.g., in the case of tarnished markers, higher resolution image generating devices offer little or no benefit. Another disadvantage is that high resolution sensors usually have a significantly smaller pixel area and, therefore, are less sensitive. The lower sensitivity of such sensors can result in potentially long exposure times and, therefore, are problematic when objects are moved.

The developers of tracking systems thus find themselves in a sort of "Catch 22"; on the one hand, the markers should not be arbitrarily enlarged, and on the other hand, the resolution should not be arbitrarily increased.

SUMMARY OF THE INVENTION

The invention provides an image generating device used with an optical tracking system, such as a medical tracking system, or the like. The image generating device can be used to determine a position of a recorded image point, and can include a light scattering effect generating means. The light scattering effect generating means can generate a fuzzy image (as opposed to the conventional approach of enlarging the markers and/or increasing sensor resolution). Through the directed and defined scattering of marker light, a greater number of pixels on a sensor can be exposed, thus providing a spatially larger amount of information on the image sensor 2. Further, when light scattering effects are generated, brightness gradients are created (e.g., the image point is projected most brightly at the location where it actually is located and the brightness abates with distance from the image point's location). This provides a gradient that can be used when ascertaining the precise position of the image point. Thus, image point determination can be more precise, even though the image as a whole is actually fuzzier due to the light scattering effect.

Using the image generating device, it is possible to use an image recording system having a relatively low resolution. Further, the markers no longer need be large, and can be very small, provided they emit or reflect a sufficient brightness to create determinable image points and scattering patterns. The invention forsakes image sharpness while making it easier to detect the image points. The information on the actual position of the image point can be achieved by combining the image resolution and dynamics (sensitivity) of the sensor and the quality of the scattering pattern. If known and specific light scattering effects are used, the total energy detected from the image point can be distributed over a number of pixels in a known pattern and at known angles.

An example of the distribution discussed above is realized in a preferred embodiment, wherein the light scattering effect generating means can be a star and/or cross effect generating means. The star and/or cross effect generating means generates star and/or cross effects in two directions that are at a predetermined angle with respect to each other (preferably an angle of 90 degrees).

Higher order star and/or cross effects also can be generated. For example, star and/or cross effects can be generated in at least three directions at a predetermined angle with respect to each other, preferably an angle of 180 degrees divided by the number of directions (e.g., having identical angular distances).

With the above embodiments, a particular advantage arises as compared to targeted, diffuse defocussing, namely that by configuring the light scattering effect generating means, it is possible to predetermine the angles at which the cross and/or star pattern are going to be generated. With such prior known angles, it can be much simpler to detect and ascertain the intersection points. As a result, it also can be much simpler to ascertain the image points themselves, since only the brightest arrangement parallel to the star beams, which forms a line of "crosshairs", need be ascertained. The projection of the image point (e.g., the marker) then can be said to be situated at the intersection point.

It should be noted that star and/or cross effect generating means are not the only conceivable light scattering effect generating means within the framework of the present invention. It is conceivable, for example, to use many and various types of soft-focus effects in order to scatter the brightness of image points uniformly and homogenously outwards, wherein the brightness decreases gradually.

The light scattering effect generating means can be formed from various embodiments. A hardware configuration, for example, could be a light scattering effect filter, such as a star and/or cross effect filter, that is arranged in front of, behind, on or in a camera lens system.

The invention can further include an optical tracking system, such as a medical tracking system including an image generating device such as has been described above. In accordance with one embodiment, such a tracking system can include an image processing unit that can ascertain the position of an image point on the basis of the light scattering pattern, in particular on the basis of the star effect lines and/or their intersection points.

In accordance with another embodiment, a tracking system includes an image generating device having at least two cameras spaced apart and an image processing unit. The image processing unit can ascertain the two-dimensional position of an image point in the image of each camera on the basis of the light scattering pattern, such as, for example, the star effect lines and/or their intersection points, and can calculate a spatial position of the image point from the ascertained two-dimensional positions.

Furthermore, the present invention also provides a method for determining the position of a recorded image point by means of an optical tracking system, such as a medical tracking system, wherein:

an image can be generated using an image generating device;

a light scattering effect, such as a star and/or cross effect, can be generated on the image for predetermined image points; and in which the position of an image point can be ascertained on the basis of the light scattering pattern projected on the image, in particular on the basis of the star and/or cross effect lines and/or their intersection points.

The position of the image point can be determined by taking into account the prior known and predetermined angles of star and/or cross effect lines with respect to each other. The star and/or cross effects can be generated in two directions that are at a predetermined angle with respect to each other, preferably an angle of 90 degrees. Additionally, the effects can be generated in at least three directions that are at a predetermined angle with respect to each other, preferably an angle of 180 degrees divided by the number of directions.

In another embodiment, the star and/or cross effects can be generated in at least a number of directions that exceeds the number of image points to be positionally ascertained by one. Using this configuration, an image point can be reliably ascertained where the highest number of effect lines intersect.

The position of the image point additionally can be ascertained on the basis of the brightness gradient of the light scattering pattern, in particular the star and/or cross effect lines, since the greatest projected brightness will be where the image point is projected.

In the following, the invention will now be explained in more detail on the basis of examples and embodiments. It may comprise all the features described herein, individually and in any combination.

The forgoing and other embodiments of the invention are hereinafter discussed with reference to the drawings.

DETAILED DESCRIPTION

The present invention can be used within the framework of image-guided, navigation-assisted medical treatment. In such treatment, a position of a patient, a medical instrument and/or a treatment apparatus can be detected with the aid of markers and a camera system (tracking system), thereby enabling image-assisted surgery.

The invention has numerous advantages, including lower overall system costs, extremely small and light markers, simplified marker detection procedures, increased accuracy, and robust/reliable marker detection.

Light scattering effects such as, for example, star and/or cross effects, are shown in FIGS. 1A, 1B, 2A and 2B. The contrasted images show the effect of a star and/or cross filter in images with a number of bright image points (spotlights). As can be seen, using such an effect on the spotlights results in a cross pattern (FIG. 1B) or a star pattern (FIG. 2B), depending on the effect arrangement. The intersection point 6 of the perpendicular beams 8 (FIG. 1B) is the center of the image point (e.g., of the spotlight) and is the brightest point.

Uncertainties about potential positions of image points can arise, for example, when the beams of different image points intersect, resulting in a number of intersection points. This problem can be solved, for example, based on the brightness or brightness gradients of the beams, or based on information of the beam shape and by using higher order star and/or cross filters, as shown for example in FIG. 2B.

Figure 5:
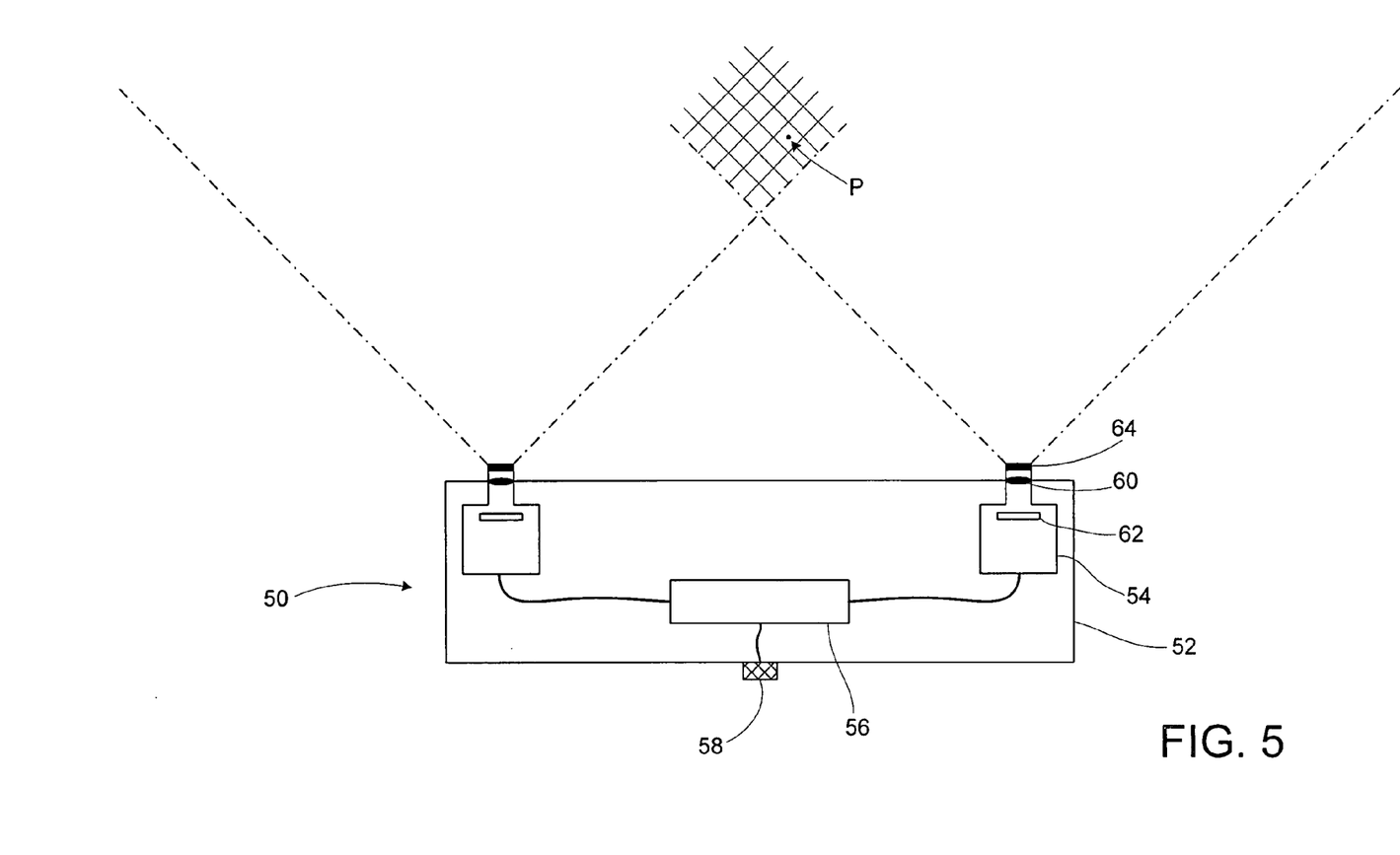
FIG. 5 is a schematic representation of an optical tracking system in accordance with an embodiment of the invention.

The star and/or cross effect can be achieved in various ways, as described previously. One example is that of using a star or cross filter, as shown in FIG. 5. FIG. 5 is a schematic representation of an optical tracking system, such as a medical tracking system 50. The tracking system 50 includes a casing 52 that is fitted with two cameras 54. Each part in FIG. 5 is only provided with a reference numeral once, even if, as with the cameras, two are provided.

The cameras 54 exhibit a common visual range indicated by crosshatching, and the tracking system 50, when calibrated, can ascertain a three-dimensional position of an image point P within a predetermined coordinate system, provided the image point is within a common visual range of the cameras 54. To this end, each camera 54 relays a two-dimensionally ascertained position to an image processing unit 56, which ascertains a three-dimensional position from the two pieces of information and outputs the three-dimensional position via an output 58. A medical navigation system, for example, can be connected to the output 58, which then enables image-guided surgery, provided markers on the patient, instruments and/or medical apparatus are positionally ascertained using the tracking system 50.

In the present embodiment, the cameras 54 each include a lens 60 that lies in front of an image sensor 2. A star and/or cross filter 64 is externally positioned in front of the lens 60. Thus, using this camera system, the image point (e.g., the indicated image point P) then can be positionally ascertained. Alternatively, the star and/or cross filter 64 can be placed directly onto the lens 60 system using suitable surface finishing techniques, or can be situated in another mold in and/or behind the lens system.

Figure 4D:
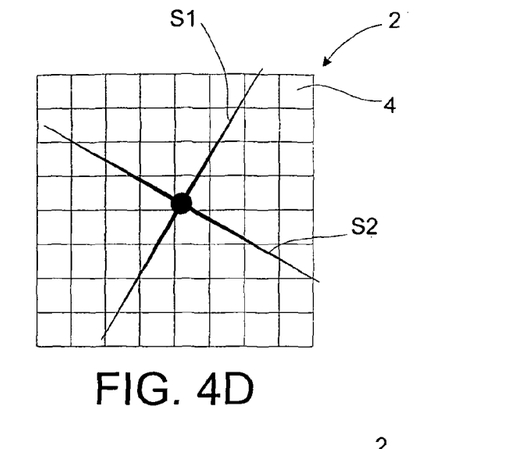
Figure 4E:
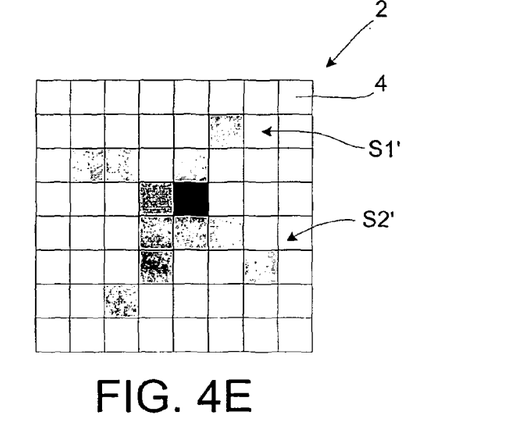
Figure 4F:
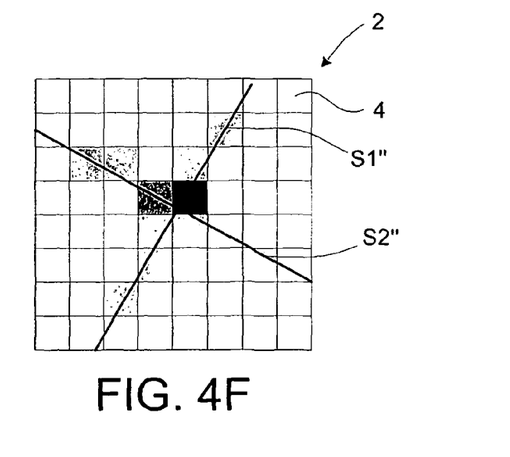

The difficulties that arise when conventionally determining the position of image points were discussed above with respect to FIGS. 4A-4C. FIGS. 4D-4F show the effect of a 4× star filter when determining the position of the same image point P (e.g., a marker), wherein beams S1 and S2 are generated by the star and/or cross filter 64 and are initially projected on the sensor 2 as a number of pixel exposures S1', S2'. As can be seen, a significantly greater number of pixels 4 are exposed on the sensor 2, and the beams S1" and S2" can in turn be ascertained from the different brightness with a significantly higher accuracy, the intersection point of the beams S1" and S2" precisely reproducing the position of the marker or image point.

Specifically, interpolating the position of the beams S1, S2 based on the brightness of the associated pixels 4 provides a much more precise estimation of the focus of the object. This is based on the fact that the orientation of the beams is known to be straight (and in this case, perpendicular to each other), and that the direction of the beams is known, since it is defined by the configuration of the star and/or cross filter 64. Object detection (segmenting) therefore can be simplified by searching for intersection points of straight lines in which the angle of the lines is already known from configuration pre-sets. The total brightness of the marker is distributed over a number of pixels 4 and, in the present case, results in a geometric pattern, wherein the intersection point of the straight lines is the center of the marker. The image of the marker can be appreciably smaller than the size of one pixel 4, since the lens 60 distributes the beam over a number of pixels 4.

Advantageously, the procedure no longer relies on algorithms that detect a marker outline and find a center point from the marker outline. The edges no longer need be detected precisely, since the center point of the marker can be calculated based on the actual brightness gradient and the shape of the exposed pixels, and additionally from the geometric intersection point information of the beams.

Based on this procedure, the size of the marker can be appreciably reduced, such that a marker can become a point with a negligible size, as long as it emits or reflects a sufficient brightness. The problem of non-uniformly illuminated, tarnished or covered markers is thus substantially eliminated.

The procedure can be based on one or more of the following assumptions.

the light source that generates the star and/or cross pattern is bright. In practice, the light source can emit or reflect infrared or UV light, such that it does not irritate the user and normal light does not disrupt detection;

the light source that generates the star and/or cross pattern can be small, such that the focus is definitively the brightness center point;

covering, wetting or tarnishing the marker and/or size tolerances are negligible, since the marker is very small with respect to such potential disruptions. If a marker is covered, it is better if the marker provides no image point rather than an incorrect image point. The missing image point, for example, can be provided by another (redundant) marker;

the image of the marker can be very small as long as it is bright enough to generate a cross pattern including a number of pixels.

The assumptions cited above are much less important than the assumptions mentioned previously for detecting the position of image points conventionally (e.g., calculating the focus), in which the shape of the marker is highly relevant.

Figure 1A:
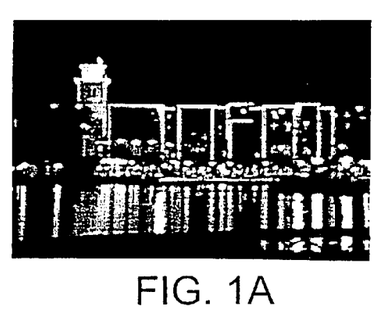
FIGS. 1A-1B and 2A-2B illustrate examples of images with and without star and/or cross effects.
Figure 1B:
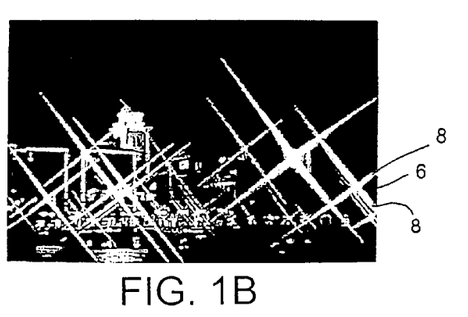
Figure 2A:
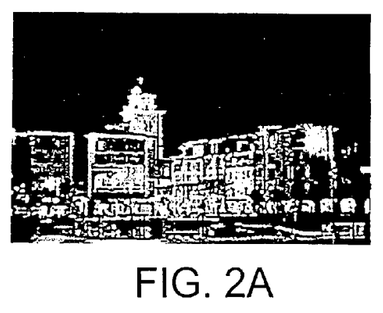
Figure 2B:
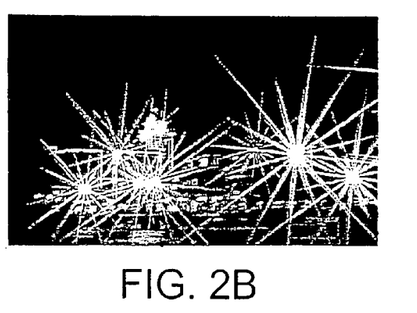
Figure 3A:
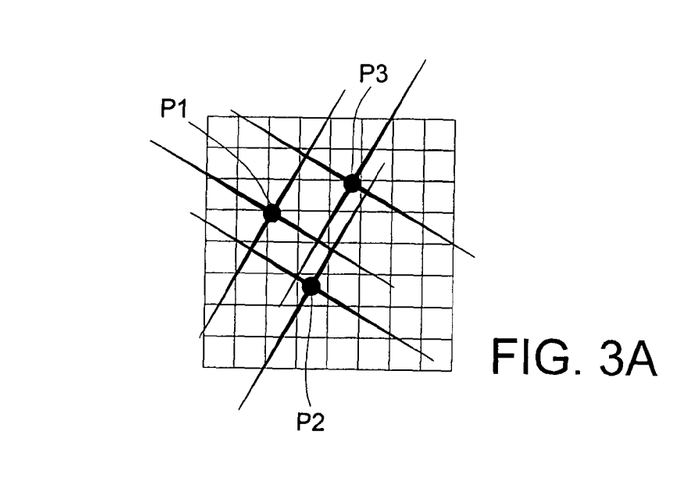
FIGS. 3A-3D illustrate examples of determining image points on camera sensors with the aid of star and/or cross effects.
Figure 3B:
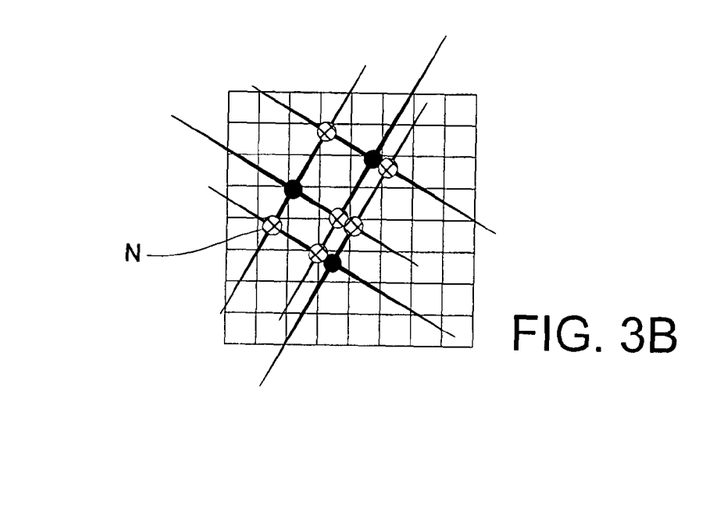

A type of excluding method has been briefly mentioned above, the excluding method preventing incorrect image points from being identified. Such an excluding method is shown again in FIGS. 3A-3D. FIG. 3A shows the correctly identified image points P1, P2 and P3 at particular intersection points of a number of light beams. FIG. 3B, however, shows that if only the intersection points are considered, a number of points would actually result, one of which is indicated as a false image point N. The false image points are indicated by crosshatching.

Figure 3C:
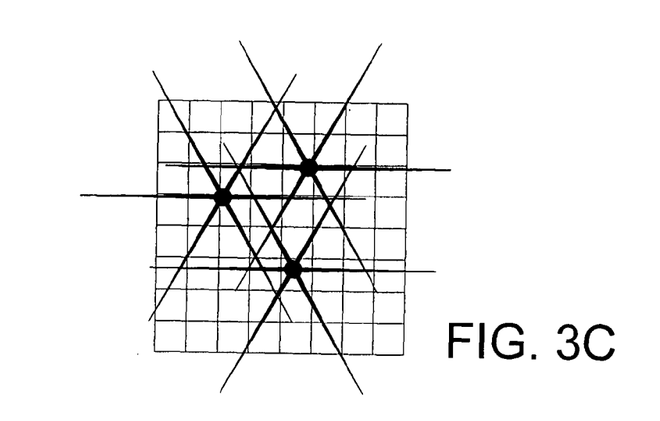

This situation could be corrected by using higher order star and/or cross filters, as for example in the image in FIG. 3C. Using this measure, it can then be said that an image point is located only where three beams intersect.

Figure 3D:
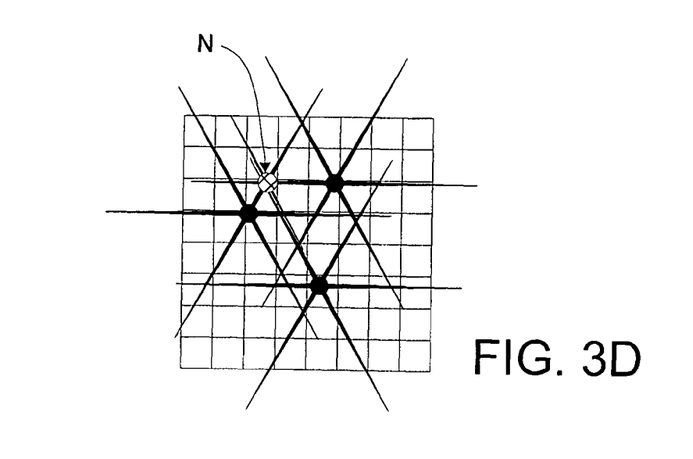

In this case, too, there still exists the possibility that uncertainties remain. Thus, FIG. 3D shows that the point N is the intersection point of three beams, even though it does not actually represent an image point. In such cases, it is useful to adduce the brightness of the point N as a whole. Because the beams decrease in brightness from the center outwards, the point N will not exhibit the same degree of brightness as the actual image points, and thus it can be excluded. Another indication of a correct marker is that the beams S1 and S2 always have the same brightness at the intersection point, as shown in FIGS. 3C and 3D. This criterion is not fulfilled by the points N in FIGS. 3C and 3D. Thus, the order of exclusion can be:

1st intersection point, 2nd intersection point of the order of the star and/or cross filter, 3rd intersection point having the highest brightness, and 4th intersection point having the same brightness as the beams.

Using the above criteria, the correct image points P1, P2 and P3 can be ascertained for each case.

The present invention is suitable for used alone or in combination with a positional marker system including at least one light-emitting or light-reflecting marker that can be positionally detected by an optical tracking system, in particular medical tracking system, wherein the emitting and/or reflecting portion of the marker or markers is formed as a point light source and/or point light reflector.

The term "point light source" includes light sources having very small dimensions, whose position can be exactly determined on a camera sensor, and whose brightness is sufficient to expose the sensor.

The emitting and/or reflecting portion of the marker or markers shall also be referred to in the following as a "point light". These point lights emit or reflect a homogenous light in an emitting direction. In other words, they output the same image from all the directions of their illuminating range.

One way of defining the size of the point lights (i.e. the size of the actually emitting and/or reflecting portion of the marker or markers) is to define the point lights via their positioning tolerance (positioning accuracy). In the field of optical tracking systems, a positioning tolerance or positioning accuracy is generally the accuracy in determining a spatial position of markers (in most cases, relative to each other, but also absolutely), wherein the point lights preferably have a size which is less than 25 times their positioning tolerance.

In an embodiment, the point lights can have a maximum size of about 3 mm, preferably about 2 mm and more preferably about 1 mm or a fraction of 1 mm. Furthermore, the point lights can have a minimum size of about 30 μm, preferably about 50 μm, more preferably about 62.5 μm.

The positional marker system preferably is configured such that the point light or point lights is/are processed and/or formed such that they emit or reflect light in a spatially uniform distribution. In one embodiment, for example, the end of a photoconductive inner part of an optical fiber is polished or burnished such that it forms a convex scattering lens.

In accordance with a preferred embodiment of the positional marker system, a number of markers comprise the ends of optical fibers fed from a common light source, wherein the light source can be an actively emitting source or a light collecting means which collects ambient light.

In another embodiment, the point lights can be reflector markers manufactured from a material that exhibits a refraction index of up to 2.4 or 2.6, in particular a diamond, rutile, fabulite, moissanite material, or the like.

In accordance with another embodiment, the point light or point lights are reflector markers made of a transparent or semi-transparent material and exhibit a crystal cut or diamond cut, such as an ideal cut, for example.

Figure 6A:
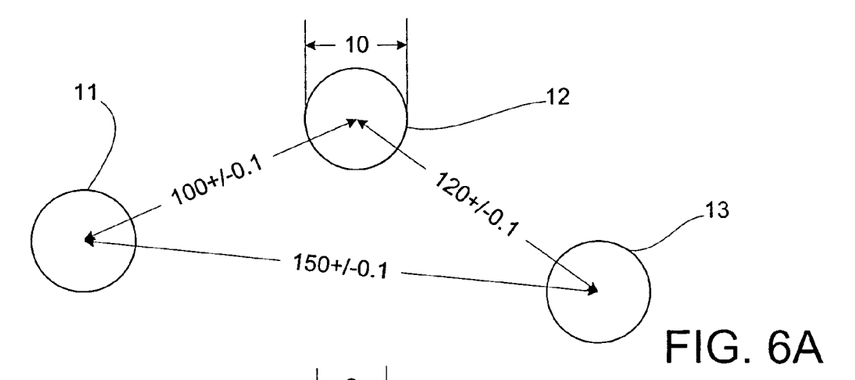
FIGS. 6A-6B are schematic diagrams illustrating a comparison of the size of conventional reflector markers and point light markers.
Figure 6B:
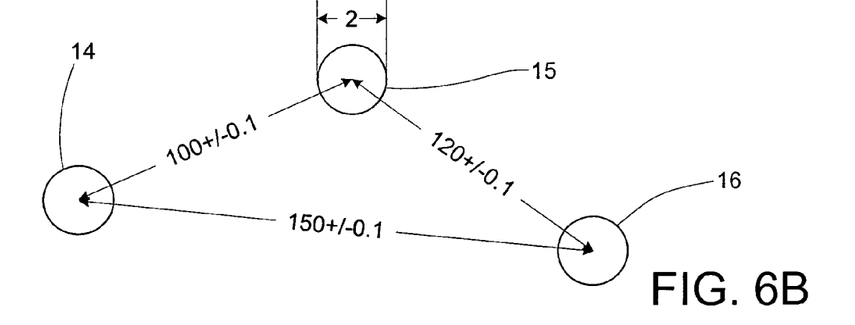

FIGS. 6A and 6B show a contrast between a conventional (FIG. 6A) and a point light positional marker system (FIG. 6B). The markers shown are the actually reflecting surface of a reflector marker 11, 12, 13. Usually, spherical or discoid retro-reflecting surfaces are used that reflect light in the output direction over a relatively large area, thereby generating a large projection of the marker in the tracking system. Three such markers, for example, can be attached to a patient's body part or on a rigid body (marker geometry), in order to ascertain its spatial position by means of a tracking system. The markers 11, 12 and 13 of the conventional marker system (FIG. 6A) exhibit different distances from each other, of 100, 120 and 150 mm, and they have a diameter of 10 mm. The positioning tolerance or positioning accuracy, e.g., the accuracy in determining the spatial position of individual markers (relative to each other, but also absolutely), is given here to ±0.1 mm. This is a typical positioning tolerance.

The markers 14, 15, 16 of the point light positional marker system shown in FIG. 6B are configured to be much smaller, wherein the actually reflecting surface can be substantially smaller. Retro-reflecting surfaces for enlarging the effective marker surface are therefore not required. In the present case, the markers have a diameter of only 2 mm and, given the same positioning tolerance and the same distances as in the conventional approach of FIG. 6A, this roughly corresponds to 20 times the positioning tolerance.

Using point light source markers results in two-dimensional positions being measured more precisely (using a camera), but also increases the three-dimensional detection accuracy when suing a stereoscopic camera system. This is due in part to the fact that a point light source marker outputs the same image from two directions with a greater probability than a relatively large marker, since mechanical deforming, covering and a non-uniform brightness distribution can be eliminated, thereby not influencing the interpolation of the position. The point light source markers, configured as individual illuminating objects, have a series of advantages. For example, the potential error when calculating or estimating the center point (focus) is in principle smaller. Further, the risk of markers being partially hidden and, therefore, incorrectly estimating the focus, is limited due to the markers being completely covered or not covered at all. If a marker is completely covered, system failure need not result since more than the required minimum number of markers for locating a single object can in principle be provided. Further, after a certain period of time a marker will no longer be covered, and thus the object can be precisely located. In medical applications, when tracking surgical instruments, for example, the size of covering objects (e.g., blood, water droplets, surgeon's fingers, etc.) will typically be larger than that of the point light marker. This ensures that a marker, only partially visible, is not incorrectly detected, which could distort determination of the position as a whole. Other advantages relate to lower weight of instruments provided with such smaller markers and to being able to integrate markers into very thin instruments, for example into catheters, drilling tools, etc.

The point light positional marker system can be an active or passive marker system, e.g., can comprise point light sources that emit light themselves or that merely reflect light. Furthermore, active systems, e.g., systems having markers that emit light, can include different light supplies. Light sources can be provided that have their own energy supply, such as, for example, a light source that is fed by a battery, a power pack, a fuel cell, a solar cell, or the like, and can be provided in a cable-free instrument that is to be located by means of the point light sources. A fiber optic cable also can be connected to the positional marker light supply using an internal or an external power supply for the light source.

Figures 7, 8, 9:
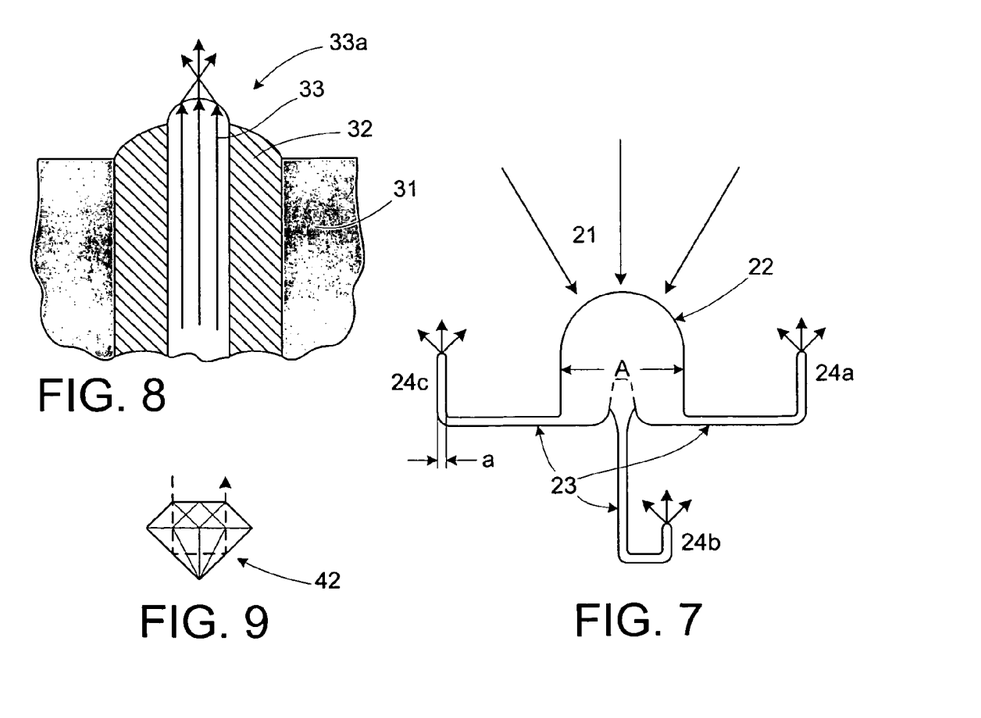
FIG. 7 illustrates an optical fiber array with a light collecting means in accordance with an embodiment of the invention.
FIG. 8 illustrates the end of an optical fiber with a point light source.
FIG. 9 illustrates a marker reflector having a diamond cut.

In one embodiment, a cable-free object, e.g., a surgical instrument, can be provided that can operate without an independent or external (e.g., electrical) power supply and which nonetheless exhibits a very high energy density of the positional marker point lights. A positional marker system for such a surgical instrument (or for surgical treatment apparatus and/or for marking patient's body parts) includes a light collecting device from which at least one optical fiber extends, the end of which forms a point light source. FIG. 7 schematically shows such an arrangement. External light 21, e.g., ambient light or light from an active light source (e.g., a constantly illuminating or intermittent light source) is collected in a relatively large collimator lens 22. In the case of medical applications, the light collecting lens 22 can be positioned at the rear or back portion of an instrument. The light collecting lens 22 can be amply supplied with visible light by surgical lights, preferably bright surgical lights, or by a separate light source that emits invisible light and/or invisible electromagnetic radiation (e.g., ultraviolet or infrared). The collimator lens 22 can be constructed such that it splits into a number of small optical fibers 23 that transport the light collected by the lens 22 to the precisely positioned point light sources 24a to 24c. The optical fibers 23 can be manufactured from a flexible or rigid plastic material or a glass material having optimized light transmission properties, such as is known from optical glass fiber data transmission lines. The brightness of the light emitted or reflected at the ends and/or the point light sources 24a to 24c is a function of the size (measurement A) of the collimator lens 22 with respect to the aperture of the point light sources 24a to 24c (measurement a), the number of optical fibers used, and the optical properties of the material used.

Based on this principle, a relatively bright point light marker can be achieved by passive illumination. As the aperture (a) is reduced in size, the light density at the ends 24a to 24c is increased. Stronger ambient light results in a higher marker brightness and therefore provides a good signal-to-noise ratio over a wide range of properties of the incident light.

As indicated above, one way of manufacturing active point light markers having a very small size is to use conventionally available fiber optic cables made of glass, plastic, or the like, such as are used, for example, in telecommunications. The photoconductive inner part of a glass fiber array typically has a size of 50 to 62.5 μm for multi-mode fibers. Optical plastic fibers are available with diameters of up to a few millimeters. The light intensity from a laser or an LED light source introduced into such a fiber is known or can be ascertained.

FIG. 8 shows one way of configuring a point light source using an optical fiber. The optical fiber 33 itself is typically surrounded by a jacket 32, which is in turn anchored in the object to be provided with the point light source, e.g., in a wall 31 of a surgical instrument. At its end 33a, the optical fiber 33 protrudes slightly out of the jacket 32. In the embodiment shown, the end 33a is polished or burnished and thus forms a convex distributor lens which outputs the light uniformly in all emitting directions.

Another way of uniformly distributing the light at the end of the fiber, for example, is to make the end of the glass or plastic fiber dispersive by implanting or placing small particles in the surface of the fiber, or by uniformly attaching recesses or grooves to the facing side of the fiber.

In another embodiment, there is provided passive point light reflectors. An advantage of such point light reflectors is that they do not require a light or a power supply and, therefore, the structures are much simpler to fabricate. Point light reflectors can be provided that can deliver a high degree of retro-reflection, and this can be enabled, for example, by using materials that exhibit a high refraction index. Such materials include, for example, diamond, rutile, fabulite, moissanite materials, or the like, which exhibit a refraction index on the order of 2.4 to 2.6. The effect is known as the "diamond effect". For materials having a high refraction index, the angle for total reflection (total inner reflection) is on the order of 24 degrees. As a result, the incident light is reflected at an extremely broad range of illumination angles.

In order to use incident light from a direction other than the viewing direction, it also is possible to use specific geometric shapes for the crystals to generate a bright light effect (e.g., a spotlight effect). This can greatly simplify the setup for a number of applications in which positional measurements are restricted by camera systems having a small size, low weight and simple handling. The marker 42 in FIG. 9 shows the classic diamond cut such as can be used to generate highly reflective effects.

Very small markers (e.g., crystals, diamonds) on the order of a fraction of a millimeter can be used and, therefore, it is not necessary to use large crystals or large crystal arrays. Such highly reflective passive point light source markers enable costs to be greatly reduced, add very little weight, and can be introduced into very small objects.

Polished or tempered metal or plastic spheres, which can be small when compared to established marker systems (see FIGS. 6A and 6B), represent another embodiment of the point light source markers. An advantage of using metal or plastic spheres is the new marker technology can be adapted to a number of instruments (e.g., surgical instruments) already in use. Other advantages are cost-effective mass production and an increased durability of the markers as compared to established markers (in particular, as compared to retro-reflective surfaces).

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An image generating device for determining a position of a recorded image point in an optical tracking system, comprising:
   a light scattering effect generating device for creating a light scattering effect;
   at least one camera operatively coupled to said light scattering effect generating device and configured to capture image data corresponding to the light scattering effect created by the light scattering effect generating device; and
   an image processing unit operatively coupled to said camera and configured to receive said image data, said image processing unit configured to determine the position of the image point based on a) the light scattering effect and b) a brightness gradient of the light scattering effect.

2. The image generating device as set forth in claim 1, wherein the light scattering effect generating device is a star and/or cross effect generating device that generates star and/or cross effects in two distinct directions, the star and/or cross effects being at a predetermined angle with respect to each other.

3. The image generating device as set forth in claim 2, wherein the predetermined angle is substantially 90 degrees.

4. The image generating device as set forth in claim 1, wherein the light scattering effect generating device is a star and/or cross effect generating device that generates star and/or cross effects in at least three directions that are at a predetermined angle with respect to each other.

5. The image generating device of claim 4, wherein the predetermined angle is substantially 180 degrees divided by the number of directions.

6. The image generating device as set forth in claim 1, wherein the at least one camera includes a light scattering effect filter arranged in front of, behind or on a lens of the camera.

7. The image generating device as set forth in claim 6, wherein the light scattering effect filter is a star and/or cross effect filter.

8. A method for determining a position of a recorded image point using an optical tracking system, comprising:
   generating an image using an image generating device;
   generating a light scattering effect on the image for predetermined image points; and
   ascertaining the position of the image point on the basis of
   a) the generated light scattering effect and b) a brightness gradient of the light scattering effect.

9. The method of claim 8, wherein generating a light scattering effect includes using a star and/or cross effects, and wherein ascertaining the position of the image point includes using the star and/or cross effect lines and/or their intersection points.

10. The method as set forth in claim 9, further comprising taking into account prior known and predetermined angles of star and/or cross effect lines with respect to each other to determine the position of the image point.

11. The method as set forth in claim 9, wherein using the star and/or cross effects includes generating the star and/or cross effects in two directions that are at a predetermined angle with respect to each other.

12. The method of claim 11, wherein the predetermined angle is substantially 90 degrees.

13. The method as set forth in claim 9, wherein using star and/or cross effects includes generating the star and/or cross effects in at least three directions that are at a predetermined angle with respect to each other.

14. The method of claim 13, wherein the predetermined angle is substantially 180 degrees divided by the number of directions.

15. The method as set forth in claim 9, wherein using star and/or cross effects includes generating star and/or cross effects in at least a number of directions that exceeds the number of image points to be positionally ascertained by 1.

16. The method of claim 8, wherein the light scattering pattern is star and/or cross effect lines.

17. The method as set forth in claim 8, further comprising determining the position of the image point on the basis of lines of the light scattering pattern having substantially the same brightness at an intersection point.

* * * * *